(12) United States Patent
Preuss et al.

(10) Patent No.: US 8,623,001 B2
(45) Date of Patent: Jan. 7, 2014

(54) CONTACT GLASS FOR OPHTHALMOLOGIC SURGERY

(75) Inventors: Dirk Preuss, Jena (DE); Elke Ebert, Jena (DE); Gregor Stobrawa, Jena (DE); Mark Bischoff, Jena (DE); Dietmar Steinmetz, Bucha (DE)

(73) Assignee: Carl Zeiss Meditec AG, Jena (DE)

( * ) Notice: Subject to any disclaimer, the term of this patent is extended or adjusted under 35 U.S.C. 154(b) by 1405 days.

(21) Appl. No.: 11/497,537

(22) Filed: Aug. 1, 2006

(65) Prior Publication Data

US 2008/0183159 A1    Jul. 31, 2008

(30) Foreign Application Priority Data

Aug. 25, 2005    (DE) .......................... 10 2005 040 338

(51) Int. Cl.
*A61B 18/18*    (2006.01)
(52) U.S. Cl.
USPC ......... 606/4; 606/5; 606/6; 606/107; 606/166
(58) Field of Classification Search
USPC ............................................................ 606/5
See application file for complete search history.

(56) References Cited

U.S. PATENT DOCUMENTS

| | | | |
|---|---|---|---|
| 4,169,664 A | | 10/1979 | Bailey, Jr. |
| 4,526,171 A | | 7/1985 | Schachar |
| 4,665,913 A | | 5/1987 | L'Esperance, Jr. |
| 4,718,418 A | | 1/1988 | L'Esperance, Jr. |
| 4,744,362 A | * | 5/1988 | Grundler ...................... 606/166 |
| 5,108,412 A | | 4/1992 | Krumeich et al. |
| 5,109,412 A | * | 4/1992 | Hollowed et al. ............. 379/455 |
| 5,171,254 A | * | 12/1992 | Sher ............................... 606/166 |
| 5,217,491 A | * | 6/1993 | Vanderbilt .................... 623/6.46 |
| 5,336,215 A | | 8/1994 | Hseuh et al. |
| 5,375,381 A | * | 12/1994 | Park et al. ....................... 52/92.1 |
| 5,549,632 A | | 8/1996 | Lai |
| 5,616,139 A | * | 4/1997 | Okamoto ........................... 606/4 |
| 5,722,952 A | * | 3/1998 | Schachar ....................... 604/506 |
| 5,772,675 A | * | 6/1998 | Hellenkamp .................. 606/166 |
| 5,984,916 A | | 11/1999 | Lai |
| 6,019,472 A | * | 2/2000 | Koester et al. ................. 351/219 |
| 6,079,826 A | * | 6/2000 | Appleton et al. .......... 351/160 R |
| 6,254,595 B1 | | 7/2001 | Juhasz et al. |

(Continued)

FOREIGN PATENT DOCUMENTS

| | | |
|---|---|---|
| DE | 103 49 297 A1 | 5/2005 |
| DE | 103 53 264 A1 | 6/2005 |

(Continued)

OTHER PUBLICATIONS

*Intralase Product Leaflet*, Essential Technology for Biomechanical Stability, Intralase Corp., 6 pgs. (2006).

*Primary Examiner* — Bill Thomson
*Assistant Examiner* — Lynsey Crandall
(74) *Attorney, Agent, or Firm* — Patterson Thuente Pedersen, P.A.

(57) ABSTRACT

A contact glass for ophthalmic surgery, including a concave anterior lens surface for placement on the eye and a suction channel annularly surrounding the periphery of the anterior lens surface. The suction channel allows the contact glass to be fixed to the eye by means of a vacuum, it is envisaged that the suction channel comprise a multiplicity of suction orifices, which are annularly arranged with respect to the anterior lens surface and through which the vacuum acts on the eye.

13 Claims, 2 Drawing Sheets

(56) References Cited

U.S. PATENT DOCUMENTS

| | | | |
|---|---|---|---|
| 6,497,700 B1 * | 12/2002 | LaHaye | 606/4 |
| 6,623,476 B2 * | 9/2003 | Juhasz et al. | 606/5 |
| 2001/0021844 A1 * | 9/2001 | Kurtz et al. | 606/5 |
| 2002/0103482 A1 | 8/2002 | Scholler et al. | |
| 2004/0220602 A1 | 11/2004 | Deng et al. | |
| 2004/0267294 A1 * | 12/2004 | Will | 606/166 |
| 2006/0129140 A1 | 6/2006 | Todd et al. | |
| 2006/0210277 A1 | 9/2006 | Dubnack et al. | |
| 2007/0010803 A1 | 1/2007 | Bischoff et al. | |
| 2007/0237620 A1 | 10/2007 | Mühlhoff et al. | |
| 2007/0253083 A1 | 11/2007 | Muhlhoff et al. | |

FOREIGN PATENT DOCUMENTS

| | | |
|---|---|---|
| EP | 1 159 986 A2 | 12/2001 |
| EP | 1 199 046 A2 | 4/2002 |
| WO | WO 0054093 A1 * | 9/2000 |
| WO | WO 02/083018 A1 | 10/2002 |
| WO | WO 03/002008 A1 | 1/2003 |
| WO | WO 2005/048895 A1 | 6/2005 |

\* cited by examiner

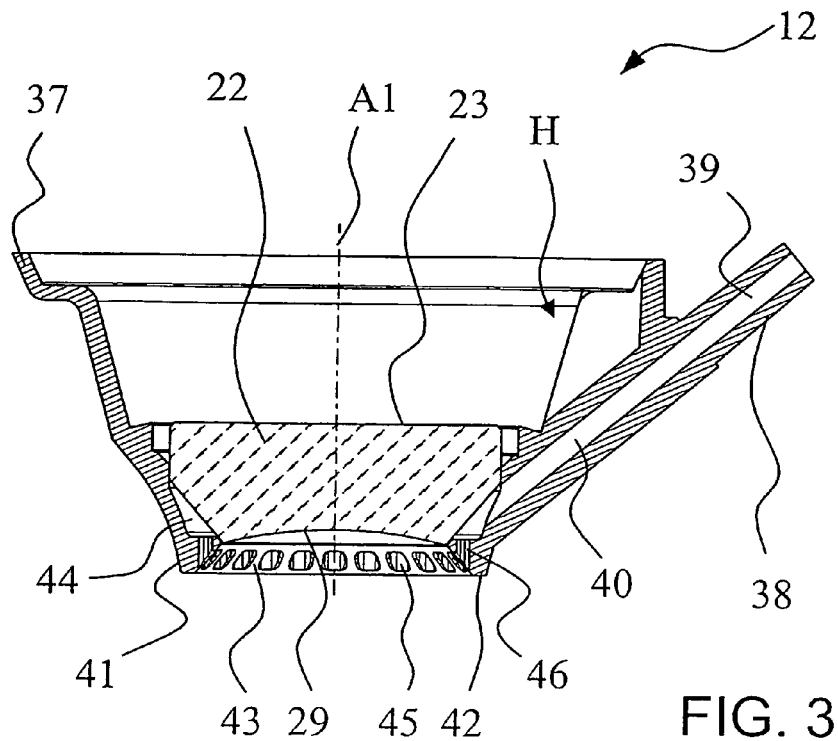
FIG. 3
FIG. 4
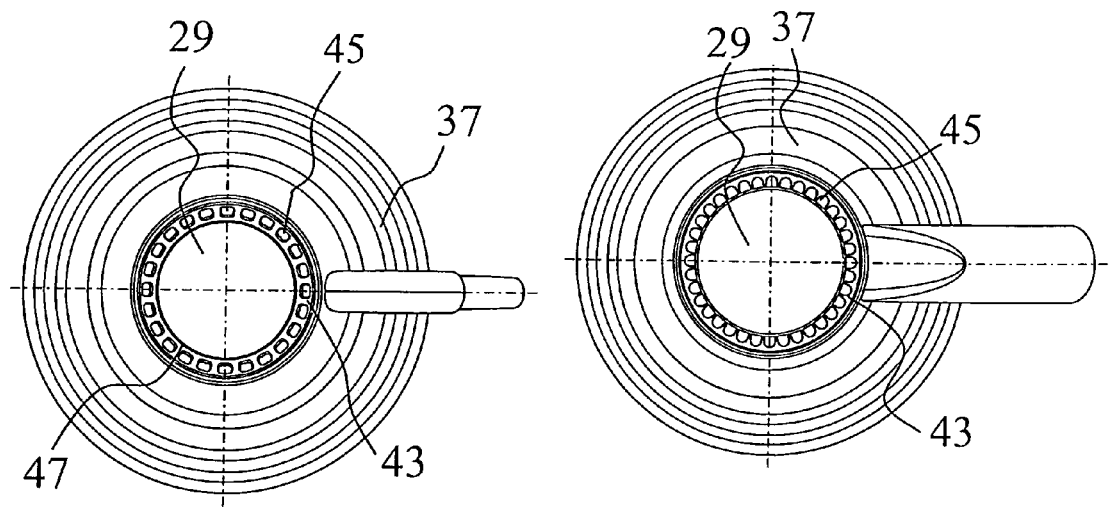
FIG. 5

CONTACT GLASS FOR OPHTHALMOLOGIC SURGERY

FIELD OF THE INVENTION

The invention relates to a contact glass for ophthalmic surgery, which glass comprises a anterior lens surface provided for placement onto the eye and means for fixing the contact glass to the eye by vacuum.

Such contact glass is shown in WO 2005/048895 A1, which otherwise deals with fixing the contact glass to a laser treatment device.

BACKGROUND OF THE INVENTION

Contact glasses in ophthalmic surgery are examples of adapters which mechanically couple the laser processing device to an object. Such coupling is required because the precision with which the laser beam is positioned in the object usually determines the precision achieved in processing. Only exact three-dimensional positioning of the laser beam in the processing volume, for example in the cornea of the eye, allows high-precision processing. Therefore, fixation of the object to be processed is effected via an adapter ensuring a precisely defined position of the object, for example of the eye, relative to the laser processing device. The adapter, which is usually referred to as contact glass, is thus part of the beam path. If the exact external shape of the object to be processed is not known, the adapter at least also functions to give the object, if possible, a certain shape which is predefined when applying a laser beam.

Since the anterior surface of the human eye's cornea varies from patient to patient, an adapter in the form of a contact glass is regularly provided in laser-assisted ophthalmic surgery. US 2001/0021844 A1 describes a corresponding contact glass which not only fixes the eye, but also deforms the anterior surface of the cornea. The US publication proposes to apply a vacuum between the cornea and the contact glass provided as a lens body, by which vacuum the eye's cornea is drawn towards the contact glass. With the lens body and the eye's cornea fixed by vacuum in this manner, the eye's cornea automatically assumes the shape of the lens body's anterior surface (anterior surface with respect to the patient). When fitting the contact glass, care must be taken to prevent the eye closing off the vacuum supply before fixing is complete. Further, this type of fixing is rather inconvenient for the patient, in particular when using the barb-shaped projections provided at the bottom surface of the lens body mount according to one embodiment of US 2001/0021844 A1, said projections being intended to achieve improved fixing of the contact glass to the eye.

Therefore, it is an object of the invention to further embody a contact glass of the above-mentioned type such that secure fixing of the lens body to the eye and reliable deformation of the cornea are effected as gently as possible for the patient.

SUMMARY OF THE INVENTION

According to the invention, this object is achieved by a contact glass of the aforementioned type, wherein the anterior surface of the lens is annularly surrounded by a multiplicity of suction orifices through which the vacuum acts on the eye.

Thus, the eye's cornea is placed in contact with the anterior surface of the lens by mechanical pressure, said mechanical pressure resulting from suction of the eye's cornea effected in a ring-shaped region surrounding the anterior surface of the lens. The ring-shaped region comprises suction orifices which supply the vacuum. This approach has two essential advantages. On the one hand, the vacuum can be applied to the eye's cornea as gently as possible. This prevents the eye's cornea being annularly sucked into an annular gap. This also prevents undesired occlusion of the suction channel. On the other hand, the patient side of the contact glass can be substantially smooth; the eye is pressed against a smooth surface provided with suction orifices. This prevents sharp edges acting on the eye, and the complicated production method required in the prior art in order to avoid sharp edges at a suction ring is now eliminated.

The vacuum applied through the suction orifices only serves to fix the eye's cornea, but does not directly cause the eye's cornea to deform, because no vacuum acts between the anterior surface of the lens and the eye's cornea. Thus, the contact glass according to the invention is particularly suitable for patients with corneal damage, anomalies or even cuts from previous ophthalmic operations that never healed in the region of the cornea to be placed in contact with the anterior surface of the lens. Since there is no vacuum acting in this region of the eye's cornea, a damaging effect can now be excluded when fixing the contact glass.

The suction orifices surrounding the anterior surface of the lens in a ring shape are preferably provided as part of a suction channel. Further, the suction orifices are favorably provided such that, when the eye fully contacts the anterior surface of the lens, they are not yet covered by the eye's cornea so that suction is not yet effected as a result. In this condition, precise positioning of the contact glass relative to the eye is possible. It is only when the contact glass is pressed further onto the eye that the eye's cornea also covers the suction orifices, whereby the vacuum fixation becomes effective.

This design of the contact glass may be achieved, for example, by the annular region in which the suction orifices located being angled relative to the optical axis and/or having a concave curvature, e.g. one which is slightly smaller than the curvature of the eye's cornea. Of course, the anterior surface of the lens may also be concave.

A convenient and particularly easy-to-produce structure of the contact glass consists in that the anterior surface of the lens is formed on a lens body held in a mount, with the suction orifices being provided in the mount. The just mentioned two-step mounting, wherein the vacuum mounting is effective only when the contact glass, in its adjusted condition, is pressed further onto the eye, can then be achieved simply if the axially forward contour of the mount does not protrude with respect to a curvature which the eye's cornea has when the eye is in full contact with the anterior surface of the lens, or if said contour even recedes relative to said curvature. That part of the mount which comprises the suction orifices will conveniently be seamlessly contiguous with the anterior surface of the lens.

Particularly easy production is achieved if the suction channel is formed between the mount and the lens body and individual channels extend from the suction channel through the wall of the mount and into the suction orifices. The suction channel may then be, for example, an annular gap between the mount and the lens body, which gap is covered by a wall of the mount on the patient's side, said wall extending from an exteriorly located edge of the mount to the edge of the anterior surface of the lens. Breakthroughs in this wall form individual channels and, thus, form the suction orifices.

The number of suction orifices is not fixed to a specific figure but will have to be selected according to the conditions of manufacture. The shape of the suction orifices may also be selected according to conditions of manufacture; in particular, they may be round, oval or rectangular. In order to prevent injuries of the eye's cornea, care should be taken, of course, to remove burrs during manufacture.

The curved surface imposed upon the eye as the desired shape by the anterior lens surface can be selected in an application-dependent manner. In particular, aspherically curved surfaces are also possible which allow optical imaging errors to be minimized when introducing treatment laser radiation.

The contact glass according to the invention allows the natural shape of the cornea to be maintained with the contact glass placed thereon, which is particularly convenient for patients. With a suitable curvature of the anterior lens surface, the eye is placed in contact with the contact glass with minimal deformations. The anterior lens surface may be spherically curved in this case, having a radius of curvature of 5-30 mm; a radius which is slightly greater than that of the human eye is preferred and therefore lies in the range from 15-25 mm.

The annularly arranged suction orifices effectively prevent parts of the eye's cornea being sucked into the upper part of the suction channel and thus partially occluding the latter. As a consequence, introduction of the vacuum into the suction channel is uncritical, because the entire suction channel is effective at all times and, in particular, the vacuum connector cannot be occluded by the eye's cornea.

The contact glass according to the invention enables particularly easy placement of the contact glass onto the eye's cornea, in particular if the curved surface of the anterior lens surface has a slightly flatter curvature than the eye's cornea. When approaching the contact glass, only the central region of the eye's cornea, i.e. the corneal vertex, touches the anterior lens surface. As placement progresses, the eye's cornea gradually contacts the full anterior lens surface, with the suction orifices still not being covered in this condition either and the patient still being able to move his eye freely in spite of partial deformation. In this condition, easy alignment of the contact glass with the eye is possible. Once the desired adjustment position is achieved, the distance between the contact glass and the patient's eye is reduced somewhat further, causing the annular gap to be closed by the cornea of the eye and causing the eye to be vacuum-fixed relative to the contact glass.

It has turned out that suction of the conjunctiva to the vacuum fixing means should be avoided during vacuum fixing of an ophthalmic contact glass, because otherwise insufficient fixing of the eye's cornea on which surgery is to be performed may occur. Regardless of how the contact glass is designed in other respects and in particular regardless of the design of the means for vacuum fixation, it is convenient to provide a contact glass for ophthalmic surgery comprising an anterior lens surface designed to be placed on the eye and means for vacuum fixture of the contact glass to the eye, and which is further characterized in that a coding element encoding a geometric or optical parameter of the contact glass is provided on the contact glass. The geometric or optical parameter is conveniently the diameter of the anterior lens surface. The coding element is favorably attached to the contact glass in a manner allowing a user, i.e. an eye surgeon, to recognize the desired geometric or optical parameter, e.g. the desired diameter of the anterior lens surface, from the outside. A suitable coding element is a bar code, a number or letter code or even a geometric or color code, for example. A contact glass bearing a color mark is particularly preferred, the color mark being assigned to the diameter of the anterior lens surface or to another geometric or optical parameter of the contact glass. If the contact glass is produced in two parts, i.e. from a lens body comprising the anterior lens surface as well as a mount holding the lens body, it will be favorable to arrange the coding element on the mount. In the case of a color code, the mount itself can be colored, for example.

In order to allow a user to select a contact glass having the desired parameters, the code is advantageously provided as an optically perceivable code, allowing a surgeon to select the desired contact glass in a quick and unerring manner.

Use of the above-described coding element is particularly advantageous, of course, in a contact glass of the type described hereinbefore or hereinafter.

BRIEF DESCRIPTION OF THE DRAWINGS

The invention will be explained in more detail below, by way of example and with reference to the Figures, wherein:

FIG. 3 shows a sectional view of a contact glass for the laser processing device of FIG. 1;

FIG. 4 shows a plan view of the contact glass of FIG. 3 from below (with respect to FIG. 3) and FIG. 5 shows a representation similar to FIG. 4 depicting a further construction of a contact glass.

DETAILED DESCRIPTION

Figure 1:
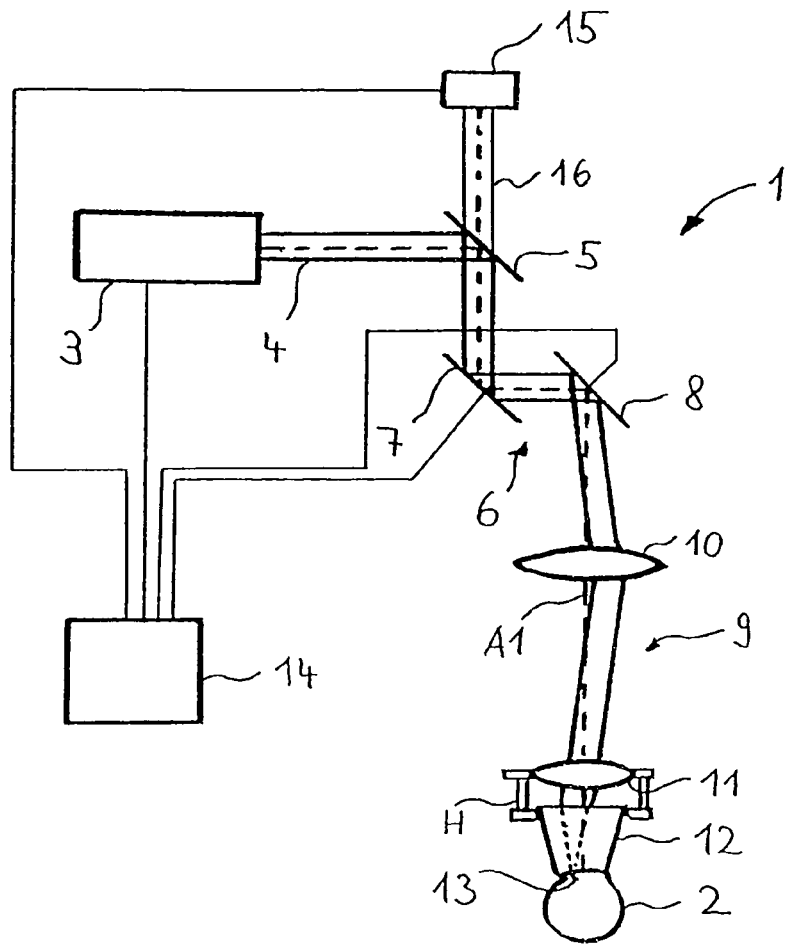
FIG. 1 shows a schematic representation of a laser processing device for ophthalmic surgery.

FIG. 1 shows a treatment device for an ophthalmic method similar to those described in EP 1159986 A1 and U.S. Pat. No. 5,549,632. The treatment device 1 of FIG. 1 serves to perform correction of an eyesight defect on a patient's eye 2 according to the known femtosecond LASIK method. For this purpose, the treatment device 1 has a laser 3 which emits pulsed laser radiation. The pulse duration is within the femtosecond range, for example, and the laser radiation acts by means of non-linear optical effects in the cornea, as described above. The treatment beam 4 emitted by the laser 3 along an optical axis A1 is incident on a beam splitter 5 which transmits the treatment beam 4 to a scanning unit 6. The scanning unit 6 comprises two scanning mirrors 7 and 8 which are rotatable about mutually orthogonal axes such that the scanning unit 6 two-dimensionally deflects the treatment beam 4. Adjustable projection optics 9 focus the treatment beam 4 onto or into the eye 2. The projection optics 9 comprise two lenses 10 and 11. The treatment device 1 is a laser processing device.

Arranged following the lens 11 is a contact glass 12 which is securely connected to the lens 11, and thus to the beam path of the treatment device 1, via a holder H. The contact glass 12, which will be explained in more detail below, contacts the cornea of the eye 2. The optical combination of the treatment device 1 with the contact glass 12 fixed thereto causes the treatment beam 4 to be focused at a focus 13 located within the cornea of the eye 2.

Like the laser 3 and the projection optics 9, the scanning unit 6 is controlled by a control device 14 via control lines (not specifically designated). The control device 14 determines the position of the focus 13 both transverse to the optical axis A1 (by the scanning mirrors 7 and 8) and in the direction of the optical axis A1 (by the projection optics 9).

The control device 14 further reads out a detector 15 which reads out radiation scattered back from the cornea and passing through the beam splitter 5 as return radiation 16. The detector 15 allows very precise control of the operation of the laser 3.

The contact glass 12 ensures that the cornea of the eye 2 obtains a desired specified shape. Due to the cornea 17 contacting the contact glass 12, the eye is located in a predetermined position with respect to the contact glass 12 and thus to the treatment device 1 connected thereto.

Figure 2:
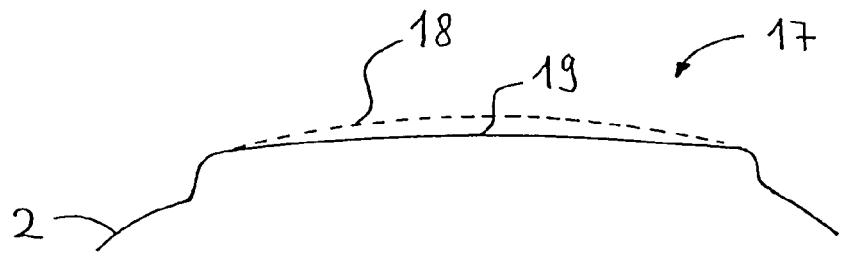
FIG. 2 shows a schematic view of a patient's cornea.

This is schematically illustrated in FIG. 2 which shows a sectional view of the eye's cornea 17. In order to achieve exact positioning of the focus 13 in the eye's cornea 17, the curvature of the eye's cornea 17 has to be considered. The cornea 17 has an actual shape 18 which differs from patient to patient. The adapter 12 contacts the eye's cornea 17 such that it deforms the latter towards a desired shape 19. The exact profile of the desired shape 19 depends on the curvature of the anterior lens surface of the contact glass that faces towards the eye 2. Known geometric and optical conditions for introducing and focusing the treatment beam 4 into the cornea 17 are given by the adapter 12. Since the cornea 17 contacts the contact glass 12, which is in turn stationary with respect to the beam path of the treatment device 1 due to the holder H, exact three-dimensional positioning of the focus 13 is achieved by controlling the scanning unit 6 as well as the adjustable projection optics 9.

FIG. 3 shows a detail of the contact glass 12 in a sectional view. The contact glass 12 has a two-part design and consists of a lens body 22, which is secured in a mount 37, e.g. by gluing. The lens body 22, which may be made of glass, for example, has a planar entrance surface 23, at which the treatment radiation from the laser treatment device 1 is supplied, and an anterior lens surface 29, which is located opposite, on the patient's side, and is adapted to the curvature of the human cornea. By pressing the contact glass 12 onto the eye's cornea 17, the anterior lens surface 29 of the lens body 22 held in the mount 37 imparts the desired shape 19 to the eye's cornea 17. The lens body 22 consists of glass or of medically approved plastics, such as PMMA or polycarbonate. These materials are also suitable for the mount, which may be additionally made of polyurethane or silicone rubber.

In order to provide the vacuum, the mount 37 comprises a port 38 which is provided with a connecting port 39, with a vacuum tube fitted thereon, as well as a vacuum supply line 40 extending inside the nozzle 38. The supply line 40 terminates laterally of the lens body 22 above an attachment ring 41 of the mount 37.

With its surface located on the patient's side (viewed from below in the illustration of FIG. 3), the attachment ring 41 continues the curvature of the anterior lens surface 29 such that the axially outermost contour of the attachment ring 41 is located, in the form of a lower edge 42, in an extension of the curvature of the anterior lens surface 29. A suction surface 43 is formed between said edge 42 and the outer edge of the anterior lens surface 29.

The suction surface 43 covers an annular suction channel 44, which is formed by a gap between the mount 37 and the lens body 22 in this embodiment. In principle, however, it would also be possible for the suction channel to be located completely within the material of the mount 37. In the embodiment shown in FIG. 3, the suction surface 37 is thus formed by a wall extending from the outermost edge 42 of the attachment ring 41 to the edge of the anterior lens surface 29. In the suction surface 43, i.e. within said wall, suction orifices 45 are formed, which constitute the patient-side ends of individual channels 46 whose other ends terminate in the suction channel 44.

Thus, through the vacuum supply line 40, a vacuum applied to the vacuum connection 39 reaches the vacuum channel 44, where it acts on the eye's cornea by means of the suction orifices 45 surrounding the anterior lens surface 29 in a ring-shaped manner.

Since the suction surface 43 preferably continues the curvature of the anterior lens surface 29 in a smooth manner (with a continuation of a spherically curved surface being possible, but also an aspherical curvature or a curvature with a radius of curvature which differs from that of the anterior lens surface 29 and is either greater or smaller), there is a largely smooth transition from the anterior lens surface 29 to the suction surface 43 on the whole. In any case, the transition has no sharp edges, but consists, at the most, of an annular boundary at which the curvature or inclination changes.

FIG. 4 shows the contact glass 12 of FIG. 3 in a view from the patient's side, i.e. from below in FIG. 3. As is clearly visible, the suction orifices 45 are oval here and surround the anterior lens surface 29 externally of a boundary 47 between the mount 37 and the lens body 22 in the region of the annular suction surface 43.

FIG. 5 shows a modified design, wherein the suction orifices 45 have a different geometric shape, namely the shape of half-ovals providing an arcade-shaped structure of the suction orifices 45. The vacuum connection is also differently designed here, namely as a Luer lock connection.

The diameter of the annular suction surface 43 and thus also of the anterior lens surface 29 is preferably selected in a patient-dependent manner. Thus, different contact glasses 12 having different diameters of the anterior lens surface 29 and thus different diameters of the annular suction surface 43 are kept in store for one single treatment device, so that the suction orifices 45 are definitely in place on the cornea of the patient receiving treatment, thus ensuring optimal suction. This avoids suction of the conjunctiva in the region of the suction surface 43. In order to make it easier for the user to distinguish between different contact glasses 12, e.g. contact glasses having different diameters of the anterior lens surface 29 (and thus of the suction surface 43) or having different radiuses of curvature, a color code is optionally provided in the region of the mount 37. It is particularly advantageous here to dye the entire mount.

For easier observation of the patient's eye when using the contact glass 12, it is possible to irradiate light from a light source through the mount 37 to the site of treatment. This is described, for example, in DE 10353264 A1. The suction surface 43 being interrupted merely in the region of the suction orifices 45 considerably facilitates coupling-in of the radiation and it is no longer required to use the optical means described in DE 10353264 A1, which are provided in order to compensate for the optical effect of an annularly opened suction channel.

When placing the contact glass on the eye's cornea, contact is established first between the anterior lens surface 29 and the corneal vertex. As the application of the eye's cornea to the anterior lens surface 29 progresses, contact with the eye's cornea is established in an increasingly large surface region of the anterior lens surface. When the eye's cornea fully contacts the anterior lens surface 29, no contact is established yet between the axially foremost contour line of the attachment ring 41 and the eye's cornea, due to the increasing curvature in the peripheral region of the eye's cornea, so that the suction orifices 45 are not yet covered by the eye's cornea. Accordingly, it is still possible in this condition to adjust the eye, which is in contact with the anterior lens surface 29, such that the optical axis A1 is located exactly as desired, e.g. coincides with the axis of vision. Only upon pressing the contact glass and the eye closer together does the eye's cornea also contact the axially foremost contour line 42 of the attachment ring 41, whereby the suction channel 44 is closed at the suction orifices 45 and the contact glass 12 is fixed to the eye.

For example, the mount 37 is designed such, with respect to the attachment ring 41, that the axially foremost contour line of the periphery 42 of the attachment ring 41 does not protrude relative to that of a curved surface defined by the curvature of the eye when the eye's cornea is in full contact with the anterior lens surface 29. In one embodiment, the periphery 42 is located exactly in the imaginary extension of the curved surface. For simplification, the curvature of the anterior lens surface 29 can also be referred to.

Of course, the geometric designs described herein can also be advantageously used individually or in other combinations not explicitly shown or described.

The invention claimed is:

1. An adapter contact lens to be applied in contact with an anterior corneal surface of a cornea of an eye, the adapter comprising:
   a contact glass portion having an anterior lens surface, adapted for placement in contact with the eye; and
   a mount portion circumferentially surrounding the contact glass portion, the mount portion presenting a plurality of suction orifices annularly surrounding the anterior lens surface of the contact glass portion, wherein the mount portion and the plurality of suction orifices are shaped and adapted to apply suction to the surface of the eye through the suction orifices;
   the mount portion further comprising a suction channel, which annularly surrounds the periphery of the anterior lens surface and in which the suction orifices terminate;
   wherein the suction channel is an annular space between and partially bounded by the mount portion and the contact glass portion, the annular space being further bounded by a wall of the mount portion extending from an exteriorly located edge of the mount portion to the edge of the anterior lens surface, and the wall of the mount further defining openings therethrough that form individual channels and, thus, the suction orifices.

2. The adapter contact lens as claimed in claim 1, wherein the anterior lens surface defines a concave curvature and the suction orifices are located on a curved annular surface.

3. The adapter contact lens as claimed in claim 1, wherein the anterior lens surface defines a concave curvature and the suction orifices are located on a curved annular surface.

4. The adapter contact lens as claimed in claim 1, wherein the suction orifices are round, oval or rectangular.

5. The adapter contact lens as claimed in claim 1, further comprising a coding element encoding a geometric or optical parameter of the contact glass.

6. The adapter contact lens as claimed in claim 5, wherein the coding element encodes a diameter of the anterior lens surface.

7. The adapter contact lens as claimed in claim 5, wherein the coding element comprises color coding.

8. The adapter contact lens as claimed in claim 1, further comprising an optical coupling to couple illumination radiation into the region of the annularly arranged suction orifices.

9. The adapter contact lens as claimed in claim 1, wherein the anterior lens surface is aspheric.

10. The adapter contact lens as claimed in claim 1, wherein the structure of the adapter contact lens is such that no vacuum is applied between an anterior surface of the contact glass portion and the eye when vacuum is applied to the mount portion.

11. The adapter contact lens as claimed in claim 1, wherein the suction orifices are provided such that, when the eye fully contacts an anterior surface of the lens body, the suction orifices are not covered by the cornea of the eye so that suction is not effected.

12. The adapter contact lens as claimed in claim 1, wherein the suction orifices are located in an anterior concave surface portion of the mount and wherein a curvature of the anterior concave surface portion is less than a standard curvature of the cornea of the human eye.

13. The adapter contact lens as claimed in claim 1, wherein an axially forward contour of the mount does not protrude with respect to a standard curvature of the cornea of the eye.

* * * * *